United States Patent [19]

McClennen et al.

[11] Patent Number: 4,970,905

[45] Date of Patent: Nov. 20, 1990

[54] APPARATUS AND METHOD FOR SAMPLING

[75] Inventors: William H. McClennen; Neil S. Arnold, both of Salt Lake City; Henk L. C. Meuzelaar, Summit Park, all of Utah

[73] Assignee: University of Utah, Salt Lake City, Utah

[21] Appl. No.: 356,983

[22] Filed: May 25, 1989

[51] Int. Cl.$^5$ ............................. G01N 1/24; G01N 1/14
[52] U.S. Cl. .............................. 73/864.34; 73/864.73; 73/863
[58] Field of Search ................ 73/863, 864.73, 864.34, 73/864.35, 863.71, 864.81–864.87, 23.1, 61.1 C, 863.83, 863.84, 863.86, 23.41

[56] References Cited

U.S. PATENT DOCUMENTS

| | | | |
|---|---|---|---|
| Re. 29,304 | 7/1977 | Greenfield et al. | 356/316 |
| 3,106,843 | 10/1963 | Luxi | 73/864.73 X |
| 3,289,481 | 12/1966 | Barnes | 73/864.73 X |
| 3,680,388 | 8/1972 | Critchley et al. | 73/864.34 X |
| 3,796,672 | 3/1974 | Dada et al. | 423/261 X |
| 4,008,620 | 2/1977 | Narato et al. | 73/864.34 |
| 4,019,863 | 4/1977 | Jenkins et al. | |
| 4,032,395 | 6/1977 | Burnette | 73/864.73 X |
| 4,266,113 | 5/1981 | Denton et al. | 356/316 X |
| 4,461,183 | 7/1984 | Wedding | 73/863.21 |
| 4,713,963 | 12/1987 | Sharp | 73/23.1 |
| 4,748,128 | 5/1988 | Katopodis | 422/61 X |

FOREIGN PATENT DOCUMENTS

| | | | |
|---|---|---|---|
| 245082 | 11/1987 | European Pat. Off. | 73/864.73 |
| 3545491 | 7/1987 | Fed. Rep. of Germany | 73/864.73 |
| 261430 | 10/1988 | German Democratic Rep. | 73/864.73 |
| 1084649 | 4/1984 | U.S.S.R. | 73/864.73 |
| 1086360 | 4/1984 | U.S.S.R. | 73/864.73 |
| 2055608 | 3/1981 | United Kingdom . | |

*Primary Examiner*—Tom Noland
*Attorney, Agent, or Firm*—Andrew C. Hess

[57] ABSTRACT

Disclosed is a sampling method and apparatus in which sampling is accompanied by the steps of inducing a sample to flow into an outer chamber and excluding the sample from an inner chamber by inducing a first pressure zone in the inner chamber such that a substantially discrete interface between the first pressure zone and sample is formed at an orifice between the outer chamber and inner chamber; sufficiently reducing the first pressure zone in the inner chamber to induce the sample to flow through the orifice between the outer chamber and inner chamber and into the inner chamber such that first pressure zone-sample interface is substantially undisturbed when it moves through the orifice between the outer chamber and inner chamber; inducing the sample to flow from the inner chamber into an inner tube having an orifice within the inner chamber which forms a pathway to a detector such that the first pressure zone-sample interface remains substantially undisturbed; inducing a second pressure zone in the inner chamber such that a substantially discrete interface between the sample and second pressure zone is formed at the inner tube orifice; and inducing the sample to move along the pathway such that the first pressure zone-sample interface and second pressure zone-sample interface are substantially maintained.

12 Claims, 4 Drawing Sheets

APPARATUS AND METHOD FOR SAMPLING

BACKGROUND OF THE INVENTION

1. Field

The invention relates to apparatus and methods for sampling, particularly high resolution qualitative and quantitative microanalysis for liquid chromatography, gas chromatography and mass spectrometry.

2. State of the Art

Both manual and automated sampling apparatus and sampling methods for gas chromatography, liquid chromatography and mass spectrometry have been utilized in the prior art. The typical manual prior art sampling apparatus and sampling method are through the use of a syringe to inject a sample through a septum into a flow of carrier material, which then transports the sample to the analytical instrumentation. The typical automated prior art sampling apparatus and sampling method are through the use of a sample loop and valve. In the simplest form, the valve is designed such that it has three separate flow pathways. In the nonsampling position, the valve is set such that a carrier material is pumped from a carrier material source through the first pathway to a detector, and the sample is pumped from a sample source through the second pathway into a sample loop and then into the third pathway, and finally exiting to a sample vent. After the sample loop is completely flushed and full of sample, the valve is rotated to the sampling position which rotates the pathways such that the first pathway connects the carrier material supply with one end of the sample loop, the second pathway connects the other end of the sample loop with the detector, and the third pathway connects the sample source to the vent. In this mode the carrier material then flows through the first pathway and into the sample loop and pushes the sample out of the loop into the second pathway and then to the detector. The third pathway allows for the bypass of sample from the sample source to the vent. After the sample volume is pushed from the loop by the carrier material to the detector, the valve is rotated back to i its initial nonsampling position to flush the carrier material from the sample loop and refill the sample loop with sample. This process is repeated for multiple sampling. In more complex forms, there are many arrangements of the valves and the pathways to provide variations for multiplicity of samples and loops such that sampling loops may be filled simultaneously and the valve rotated through a multiplicity of sampling positions. Additionally, there are combinations which allow for flushing and backflushing of the valve, pathways and sampling loop between sampling.

The sampling apparatus and sampling methods of the prior art exhibit many limitations, especially when applied to microanalytical techniqes. The prior art apparatus requires a valve with moving parts and pathways through which sample flows. When switching the direction of flow between various pathways, leaks may develop if good seals are not made, or the moving parts may be subject to damage by foreign matter which may be introduced into the valve with the sample or carrier material. If the sample consists of a corrosive material, the corrosive material may also damage the sampling apparatus. Furthermore, the valves are not such that they can be made of the same inert materials of which the detector into which the sample is being injected is made. Therefore, portions of the sample may be absorbed by the sampling apparatus or foreign material may be leached out of the sampling apparatus into the sample.

Because of these construction material limitations, prior art sampling apparatus often have an upper operating temperature of approximately 250° C. At temperatures beyond 250° C. the materials used in constructing the sampling apparatus may be damaged. Since the size of the sample loop is typically set to a specific length of tubing, the sample volume is not easily varied. The amount of sample required to flush the sample loop and fill it requires a relatively large amount of sample volume, and results in relatively long sampling cycles.

The relatively long sampling cycles result in the sample being in extended contact with the carrier material during which diffusion between the sample and carrier material occurs. This perturbation of the sample results in the reduction in the qualitative and quantitative resolution of sample components.

SUMMARY OF THE INVENTION

1. Objectives

It is an objective of the invention to provide a sampling method and apparatus which is useful in both micro- and macro-analytical techniques, particularly those for gas chromatography, liquid chromatography and mass spectrometry. Other objectives of the invention are to provide a sampling method and sampling apparatus in which no moving parts come in contact with the sample, which can be operated over a broad temperature range, and in which an easily variable sample volume can be utilized. Another objective of the invention is to provide a sampling apparatus in which the apparatus may be constructed of the same inert materials as the detecting instrumentation, thereby reducing sorption of sample on or into the sampling apparatus and leaching of impurities from the sampling apparatus into the sample. Further objectives of the invention are to provide a sampling method and sampling apparatus in which very small sample volumes may be used and repetitive sampling can be performed rapidly. A further objective of the invention is to provide a sampling apparatus and sampling method in which the sample is relatively unperturbed in the sampling process thereby producing a well defined sample pulse and yielding high qualitative and quantitative resolution in the analytical results. A final objective of the invention is to provide a sampling method and apparatus in which isokinetic sampling may be accomplished.

2. Features

In the accomplishment of the foregoing objectives, the invention is a sampling apparatus and sampling method in which sampling is generally accomplished by regulating pressure between the external sample environment, the inside of the sampling apparatus, and the final pathway to a detector. The sampling apparatus comprises an inner tube having an inner orifice at one end which forms a pathway for sample flow from the sampling apparatus to a detector and then a vent; a means for inducing sample flow through the inner orifice and through the pathway; a middle tube having a middle orifice at one end and a closure at the other end through which the inner tube passes which forms an inner chamber that surrounds the inner tube and inner orifice; a means for inducing pressure in the inner chamber; a means for inducing sample flow through the middle orifice and through the inner chamber; an outer tube having an outer orifice at one end and a closure at the other end through which the middle tube passes which forms an outer chamber that surrounds the middle tube and middle orifice; and a means for inducing sample flow through the outer orifice and through the outer chamber.

The sampling method comprises the steps of inducing a sample to flow into an outer chamber and excluding the sample from an inner chamber by inducing a first pressure zone in the inner chamber such that a substantially discrete interface between the first pressure zone and sample is formed at an orifice between the outer chamber and inner chamber; sufficiently reducing the first pressure zone in the inner chamber to induce the sample to flow through the orifice between the outer chamber and inner chamber and into the inner chamber such that first pressure zone-sample interface is substantially undisturbed when it moves through the orifice between the outer chamber and inner chamber; inducing the sample to flow from the inner chamber into an inner tube having an orifice within the inner chamber which forms a pathway to a detector such that the first pressure zone-sample interface remains substantially undisturbed; inducing a second pressure zone in the inner chamber such that a substantially discrete interface between the sample and second pressure zone is formed at the inner tube orifice; and inducing the sample to move along the pathway such that the first pressure zone-sample interface and sample second pressure zone interface are substantially maintained.

THE DRAWING

DETAILED DESCRIPTION OF THE ILLUSTRATED EMBODIMENT

Figure 1:
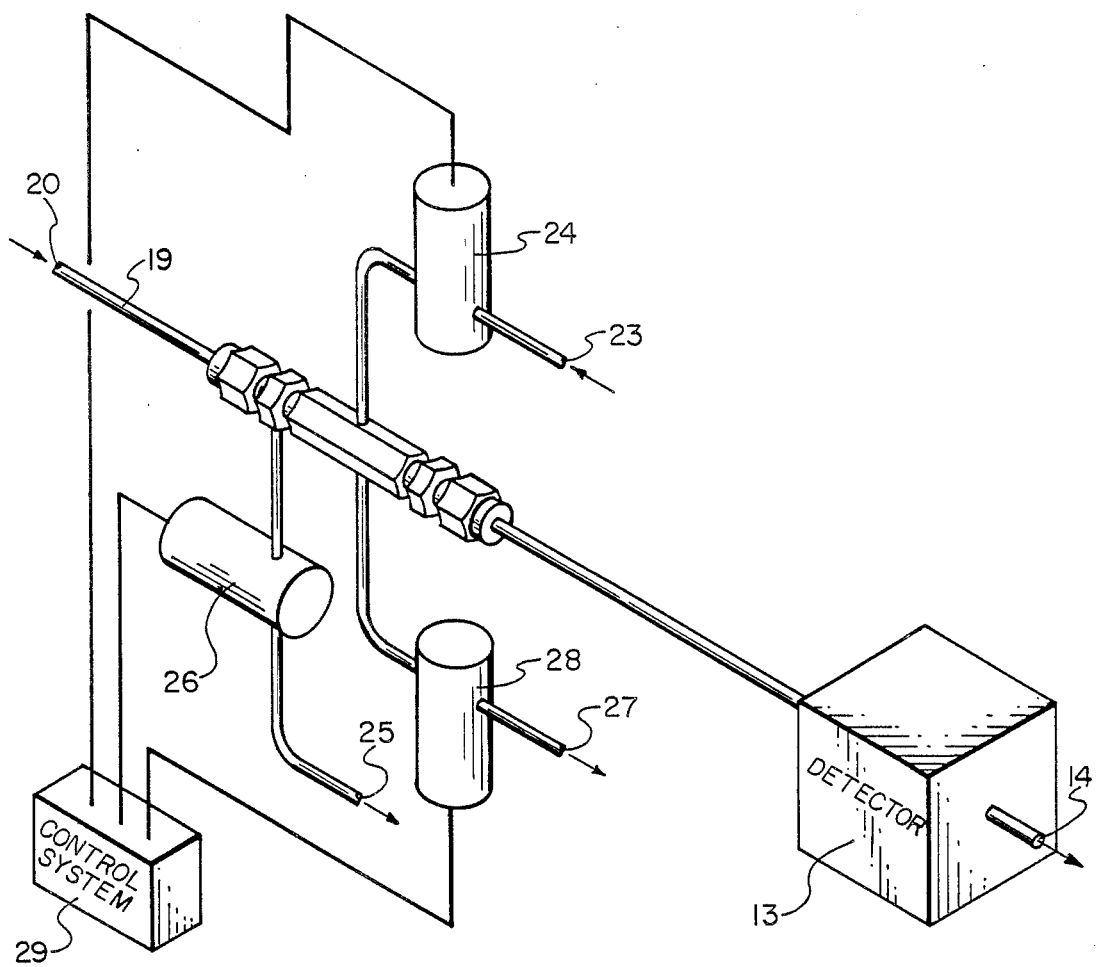
FIG. 1 is a perspective view of an embodiment of the sampling apparatus and a representation of a detector and control system.
Figure 2:
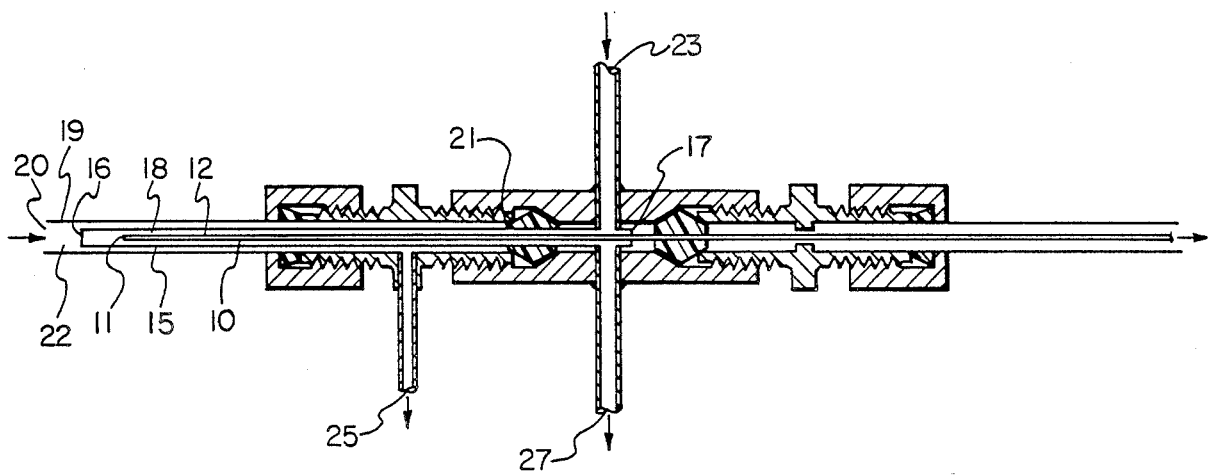
FIG. 2 is a vertical section of a portion of the sampling apparatus of FIG. 1.
Figure 3:
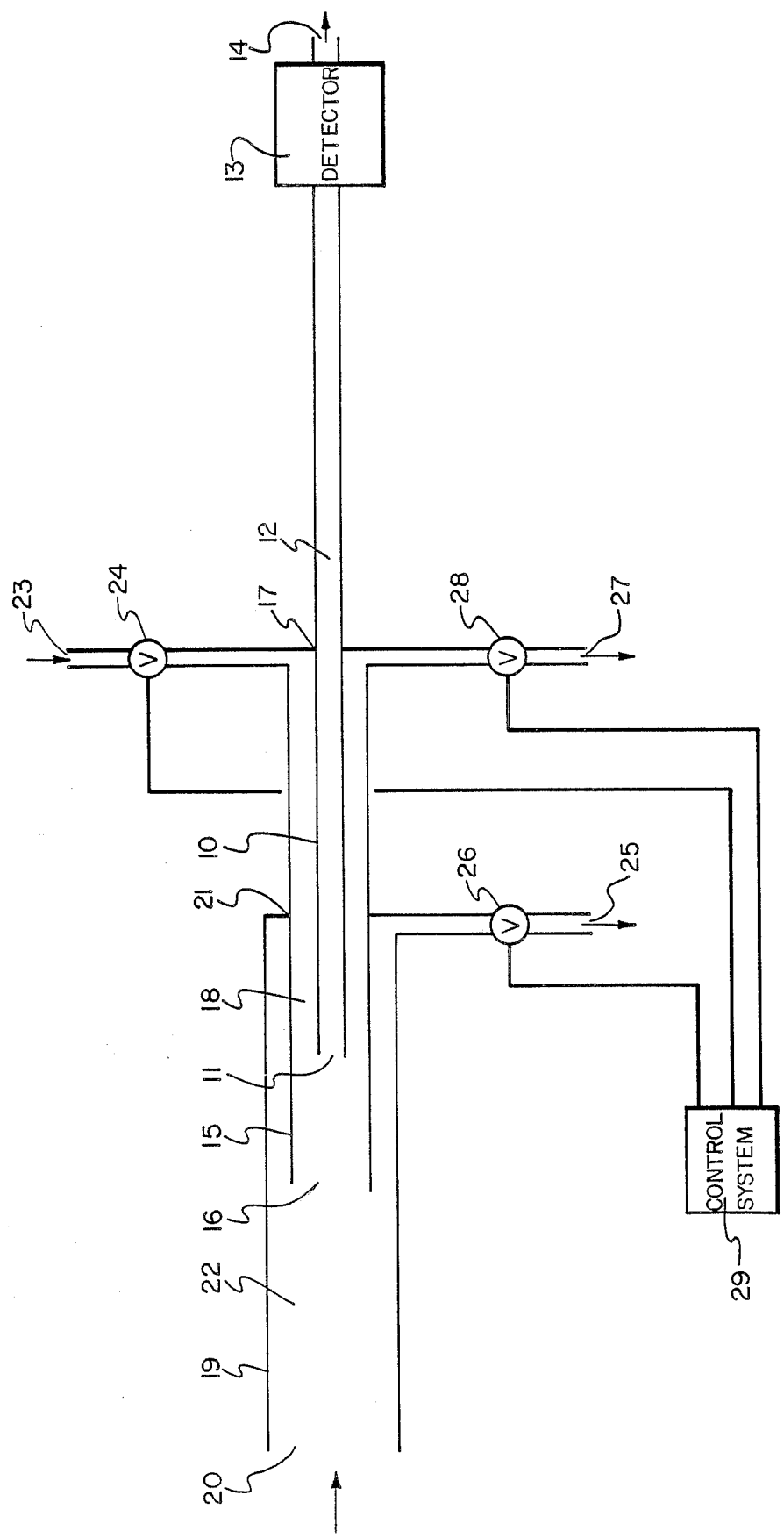
FIG. 3 is a schematic drawing of the sampling apparatus.

Referring to FIG. 1, FIG. 2 and FIG. 3, an inner tube 10 having an inner orifice 11 at one end forms a pathway 12 to a detector 13 and a vent 14. In certain applications it may be desirable to regulate the flow through pathway 12 Depending upon the particular application, such flow regulation may be accomplished by inserting, either before or after the detector, a valve or flow restricting means in pathway 12, which is not illustrated. A middle tube 15 having a middle orifice 16 at one end and an inner seal 17 at the other end through which inner tube 10 passes surrounds inner tube 10 and inner orifice 11 to form an inner chamber 18. An outer tube 19 having an outer orifice 20 at one end and an outer seal 21 at the other end through which middle tube 15 passes surrounds middle tube 15 and middle orifice 16 to form an outer chamber 22. Associated with outer chamber 22 is a means for inducing sample from the environment which is external to outer tube 19 to flow through outer orifice 20 and into outer chamber 22. Associated with inner chamber 18 is a means for inducing pressure in inner chamber 18 sufficient to exclude sample from entering inner chamber 18 through middle orifice 16. Also associated with inner chamber 18 is a means for inducing sample flow through middle orifice 16 and inner chamber 18. Associated with inner tube 10 is a means for inducing sample flow through inner orifice 11, pathway 12, detector 13 and vent 14.

Preferably the means for inducing pressure in inner chamber 18 is the introduction of an inert material through inner chamber inlet 23, with the flow of the inert material being regulated with inner chamber inlet valve 24. If the pressure of the sample environment external to outer tube 19 is greater than the pressure within the sample apparatus, the preferable means for inducing sample flow through outer orifice 20 and into outer chamber 22 is accomplished by venting the sample through outer chamber outlet 25 and regulating the flow by adjusting outer chamber outlet valve 26. Likewise, associated with inner chamber 18 is an inner chamber outlet 27 through which sample flow may be vented and regulated through inner chamber outlet valve 28. If the pressure of the sampling environment external to outer tube 19 is equal to or less than the pressure in the sampling apparatus, sample flow through outer orifice 20, outer chamber 22, middle orifice 16, inner cchamber 18, inner orifice 11 and pathway 12 may be induced by applying a vacuum to outer chamber outlet 25, inner chamber outlet 27, and vent 14. The amount of vacuum applied to outer chamber 22 and inner chamber 18 may be regulated through outer chamber outlet valve 26 and inner chamber outlet valve 28.

The preferred means for inducing sample flow through middle orifice 16 and inner chamber 18 is by decreasing the pressure within inner chamber 18 such that it is less than the pressure in outer chamber 22 by regulating the flows of the inert material into inner chamber 18 through inner chamber inlet 23 and the outflow of material from inner chamber 18 through inner chamber outlet 27 through venting or, if necessary, applying a vacuum to inner chamber outlet 27. The means for inducing sample flow through inner orifice 11 and pathway 12 to detector 13 is to allow the venting of material through vent 14 if the external sampling environment pressure is greater than the pressure at vent 14, or to apply a vacuum to vent 14 if the pressure at vent 14 is equal to or greater than the pressure in inner chamber 18. Preferably inner chamber inlet valve 24, outer chamber outlet valve 26, inner chamber outlet valve 28 and, if present, pathway 12 valve are infinitely variable valves which are regulated through control system 29.

Preferably, the various components of the sampling apparatus, or at least the surfaces thereof which may come into contact with sample, are constructed of the same inert material of the detector and instrumentation being used in the desired analysis. In the case of gas chromatography, this material is usually a fused silica. Inner tube 10, inner orifice 11, middle tube 15, middle orifice 16, outer tube 19 and outer orifice 20 may take on a variety of shapes and dimensions. However, the preferred construction is a series of concentric cylinders. Although it is contemplated in the illustrated embodiment that the tubes are connected to one another with a seal, the sampling apparatus could be molded, cast, blown or the like in an integral piece which does not have separate seals between the various components. It is also understood that the inner tube and pathway may, in certain applications, be an analytical column so that the sample passes directly on to an analytical column from inner chamber 18, and that a valve may be any type of pressure or flow regulator. It is also possible to merge inner chamber inlet 23 and inner chamber outlet 27 into a combination inlet-outlet which utilizes a tee to connect it to inner chamber inlet valve 24 and inner chamber outlet valve 28. The sampling apparatus and sampling method discussed herein are adaptable to many different analytically techniques and instruments including, but not limited to, gas chromatography, liquid chromatography, mass spectrometry and high resolution gas chromatography and mass spectrometry.

Figure 4A:
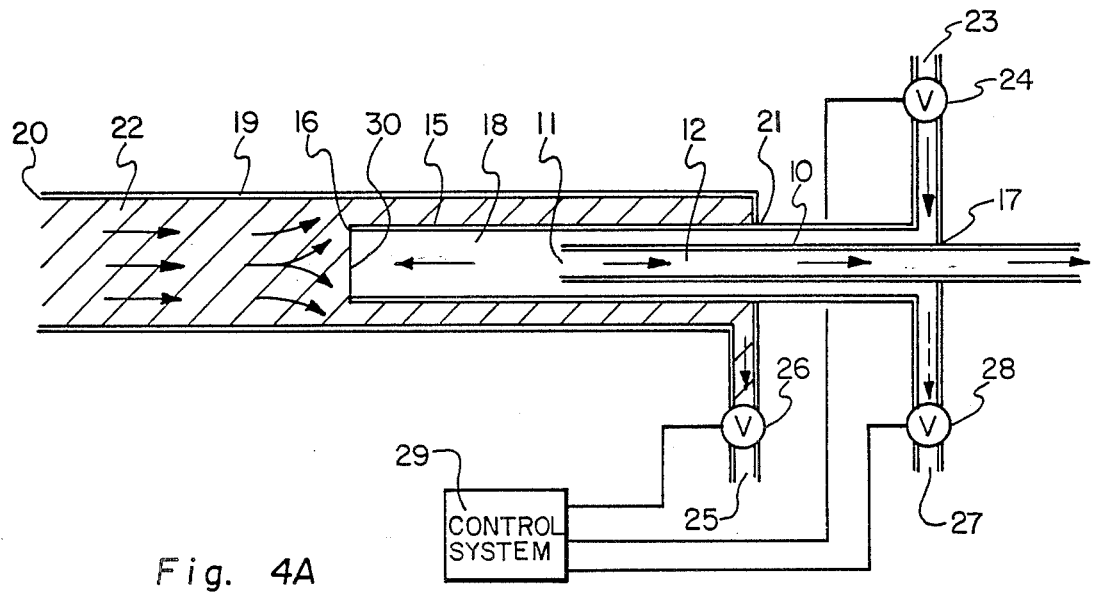
FIG. 4A is a schematic demonstrating the nonsampling mode of the sample method.
Figure 4B:
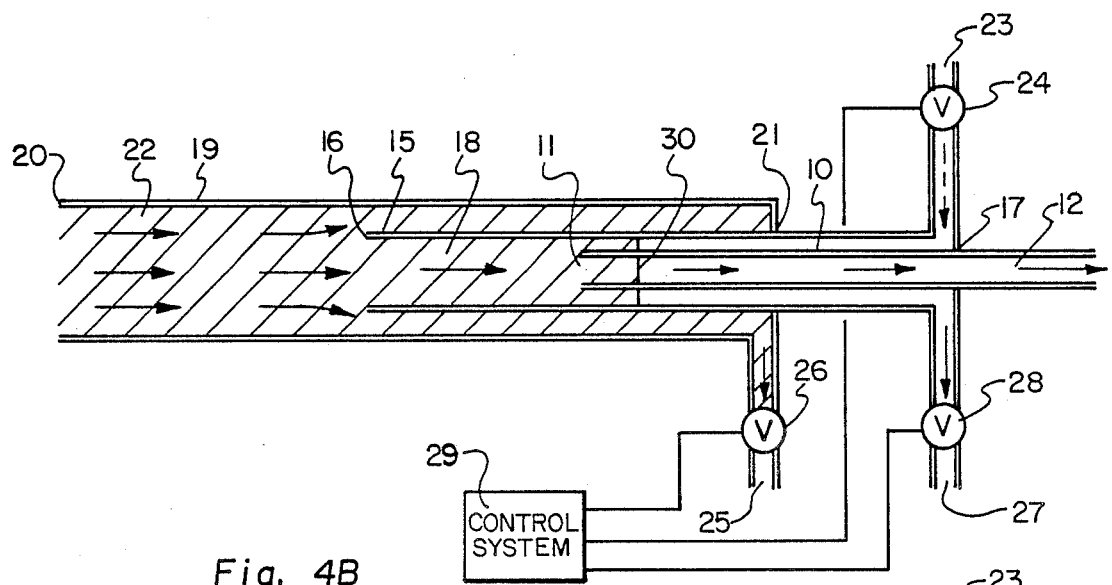
FIG. 4B is a schematic demonstrating the initial phase of sampling of the sample method.
Figure 4C:
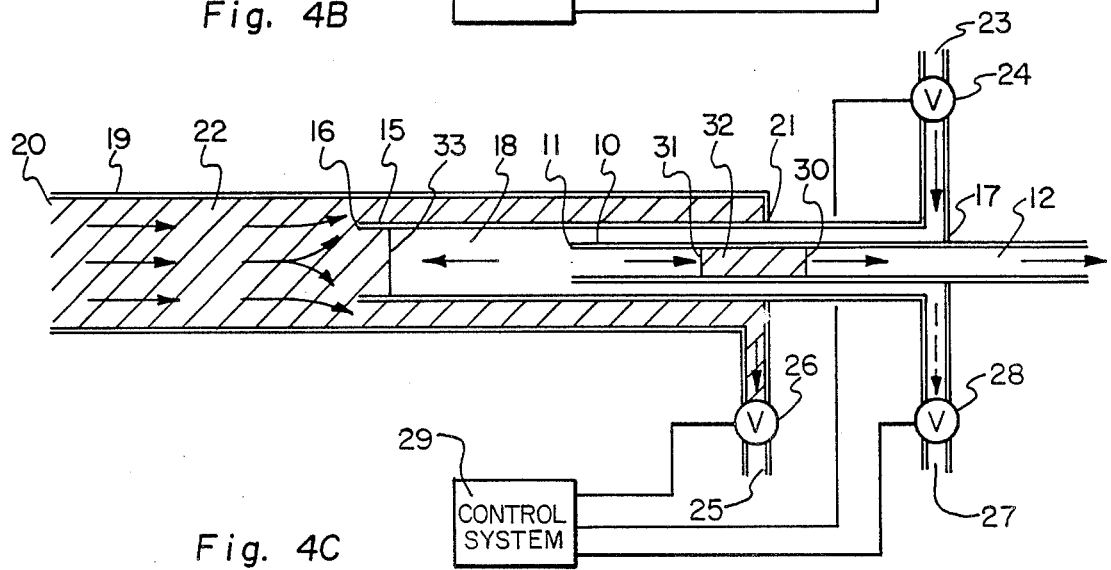
FIG. 4C is a schematic demonstrating the final phase of sampling of the sample method.

FIG. 4A, FIG. 4B, and FIG. 4C schematically depict the steps of sampling method of the invention. In these FIGURES the shaded areas represent sample, the non-shaded areas represent inert material, and the arrows represent flow direction.

Referring to FIG. 4A, in the first step of the sampling method, the nonsampling phase, sample flow from the environment external to outer tube 19 is induced through outer orifice 19 into outer chamber 22. If the pressure in the sample environment external to outer tube 19 is greater than the pressure in outer chamber 22, the sample flow is preferably induced by allowing sample to escape through outer chamber outlet 25, the sample flow being regulated by outer chamber outlet valve 26. If the pressure in the sample environment external to outer tube 19 is equal to or less than the pressure in outer chamber 22, sample flow is preferrably induced by applying a vacuum to outer chamber outlet 25, the vacuum and sample flow being regulated by outer chamber outlet valve 26. In the nonsampling phase, sample is also excluded from inner chamber 18 and pathway 12 by inducing a first pressure zone in inner chamber 18 which is greater than the sample pressure in outer chamber 22 such that a substantially discrete first pressure zone-sample interface 30 is formed at middle orifice 16.

Referring to FIG. 4B, in the second step of the sampling method, the initial phase of sampling, the first pressure zone in inner chamber 18 is reduced sufficiently to induce sample flow through middle orifice 16 into inner chamber 18 such that the first pressure zone-sample interface 30 moves through middle orifice 16, inner chamber 18, inner orifice 11, and into pathway 12 substantially undisturbed. Preferably, the advancement of sample and the first pressure zone-sample interface 30 is accomplished by reducing the inert material flow through inner chamber inlet 23 by adjusting inner chamber inlet valve 24 and simultaneously increasing the flow of material out of inner chamber 18 through inner chamber outlet 27 by adjusting inner chamber outlet valve 28. To induce this substantially undisturbed advancement of the first pressure zone-sample interface 30 and sample, it may be necessary to apply a vacuum to inner chamber outlet 27 and vent 14 and regulate the vacuum with inner chamber outlet valve 28 and an optional vent 14 valve which is not illustrated. This initial phase of sampling is continued until the desired sample size has entered pathway 12.

Referring to FIG. 4C, in the third step of the sampling method, the final phase of sampling, a second pressure zone is introduced into inner chamber 18 such that a substantially discrete sample-second pressure zone interface 31 is formed at inner tube orifice 11 thereby forming a sample plug 32 between the first pressure zone-sample interface 30 and sample-second pressure zone interface 31.

In the fourth step of the sampling method the sample plug 32 is induced to move along pathway 12 to detector 13 such that the first pressure zone-sample interface 30 and sample-second pressure zone interface 31 are substantially maintained. A second pressure zone-sample interface 33 is established at middle orifice 16 which is analogous to the first pressure zone-sample interface. Once the second pressure zone-sample interface is established, the sampling method can be repeated.

The following example of the sampling apparatus and sampling method demonstrates the invention with respect to a particular application and in no way limits the inventive concepts disclosed herein.

EXAMPLE I

Figure 5:
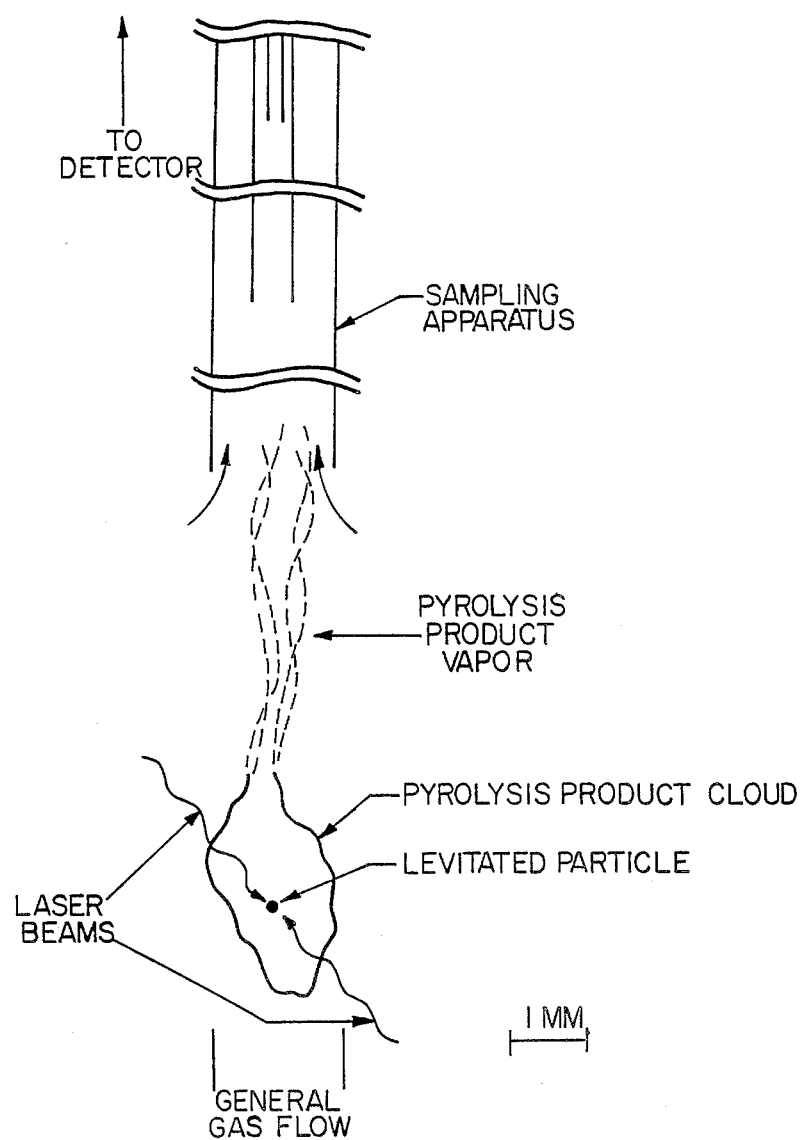
FIG. 5 is a schematic representation of Example I.

Referring to FIG. 5, a laser pyrolysis mass spectrometry experiment was designed to study the devolatilization behavior of individual coal particles at high heating rates ($10^4$–$10^6$ K/s), characteristic of pulverized coal combustion reactors. The experimental set-up consists of an electrostatic particle levitation cell, also known as an "electrodynamic balance", a 50 W cw $CO_2$ laser and a Finnigan-MAT ITMS system.

The particle levitation cell was constructed by modifying a regular ion trap electrode assembly in such a way as to provide line-of-sight access to the center of the cell for the $CO_2$ laser beam as well as for visual observation by means of a stereo microscope. Typical cell operating parameters for levitating a 120 um diameter Spherocarb particle are: ring electrode 3000 V (60 Hz ac), upper end-cap $+100$ V dc, lower end-cap $-100$ V dc.

The $CO_2$ laser (Apollo 3050 OEM) is capable of electronic pulsed beam operation. The 8 mm dia. beam is split equally into 2 opposing beams focussed at the center of the levitation cell (beam waist ca. 400 um, power density ca. 4–10 MW/m$^2$), as a co-linear parfocal HeNe laser beam permits positioning the levitated particle in the optical and electrical center of the cell. Two IR detectors measure the integrated pulse and time-resolved pulse energy.

Figure 6:
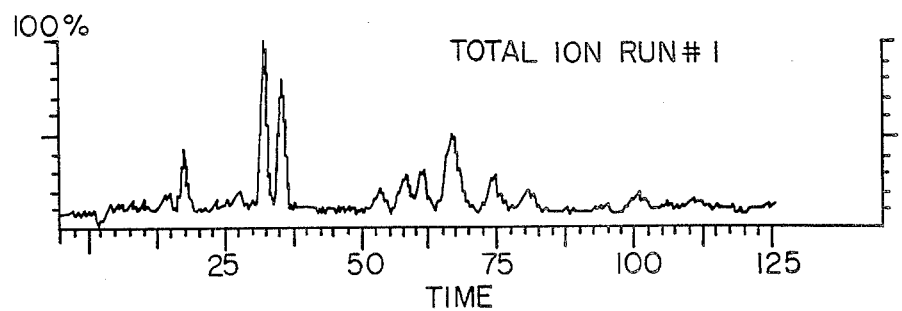
FIG. 6 is a total ion intensity vs. time gas chromotogram produced in Example I.

A heated transfer line column (2m$\times$0.18 mm DB5) equipped with the sampling apparatus enables intermittent sampling of volatiles from the center of th levitation cell into the ITMS vacuum. Feasibility studies were performed on 120–150 um Spherocarb particles impregnated with ng amounts of an alkylnaphthalenes mixture and heated with a single 10 ms $CO_2$ laser pulse. Ample signal intensities were obtained with the first laser pulse to permit the recording of "transfer line" GC/MS profiles. By contrast, a second laser pulse produced less than 10% of the volatiles observed after the first pulse, thereby demonstrating nearly complete devolatilization of the impregnated particle by a single laser pulse. FIG. 6 is a total ion intensity vs. time gas chromatogram which shows the quantitative separation of the alkylnaphthalenes in this example. In this example the sampling apparatus and method facilitated the detailed product analysis of the transient devolatilization event by its controlled sampling of a micro volume at the exact time of interest.

Whereas the invention is here illustrated and described with specific reference to an embodiment thereof presently contemplated as the best mode in carrying out such invention, it is to be understood that various changes may be made i adapting the invention to different embodiments without departing from the broad inventive of concepts disclosed herein and comprehended by the claims that follow.

We claim:

1. A sampling apparatus comprising:
   (a) an inner tube having an inner orifice at one end which forms a pathway for sample flow away from the inner orifice;
   (b) a means for inducing sample flow through the inner orifice and through the pathway;
   (c) a middle tube having a middle orifice at one end and a closure at the other end through which the inner tube passes which forms an inner chamber that surrounds the inner tube and inner orifice;
   (d) a means for inducing pressure in the inner chamber;
   (e) a means for inducing sample flow through the middle orifice and through the inner chamber;
   (f) an outer tube having an outer orifice at one end and a closure at the other end through which the middle tube passes which forms an outer chamber that surrounds the middle tube and middle orifice; and
   (g) a means for inducing sample flow through the outer orifice and through the outer chamber.

2. A sampling apparatus as recited in claim 1 wherein the means for inducing pressure in the inner chamber is through the introduction of an inert material into the inner chamber.

3. A sampling apparatus as recited in claim 2 wherein the means for inducing sample flow through the middle orifice and through the inner chamber is by applying a vacuum to the inner chamber through an inner chamber outlet.

4. A sampling apparatus as recited in claim 3 wherein the means for inducing sample flow through the outer orifice and through the outer chamber is by applying a vacuum to the outer chamber through an outer chamber outlet.

5. A sampling apparatus as recited in claim 4 wherein the means for inducing sample flow through the inner orifice and through the pathway is by applying a vacuum to the pathway.

6. A sampling apparatus as recited in claim 5 wherein the induction of pressure into the inner chamber and the vacuum applied to the inner chamber, outer chamber and pathway are regulated through separate valves attached to the inner chamber inlet, inner chamber outlet, outer chamber outlet and pathway.

7. A sampling apparatus as recited in claim 6 wherein the separate valves are regulated by a control system.

8. A sampling apparatus as recited in claim 4 wherein the induction of pressure into the inner chamber and the vacuum applied to the inner chamber and outer chamber are regulated through separate valves attached to the inner chamber inlet, inner chamber outlet and outer chamber outlet.

9. A sampling apparatus as recited in claim 8 wherein the separate valves are regulated by a control system.

10. A method for sampling comprising the steps of:
    (a) inducing a sample flow into an outer chamber and excluding the sample from an inner chamber located within the outer chamber by inducing a first pressure zone in the inner chamber such that a substantially discrete first pressure zone-sample interface is formed at an orifice between the outer chamber and inner chamber;
    (b) sufficiently reducing the first pressure zone in the inner chamber to induce the sample to flow through the orifice between the outer chamber and inner chamber into the inner chamber such that the first pressure zone-sample interface is substantially undisturbed when it moves through the orifice between the outer chamber and inner chamber and through the inner chamber;
    (c) inducing the sample to flow from the inner chamber into an inner tube which forms a pathway having an inner tube orifice positioned within the inner chamber such that the first pressure zone-sample interface remains substantially undisturbed;
    (d) inducing a second pressure zone in the inner chamber such that a substantially discrete sample-second pressure zone interface is formed at the inner tube orifice; and
    (e) inducing the sample to move along the pathway such that the first pressure zone-sample interface and sample-second pressure zone interface are substantially maintained.

11. A method for sampling as recited in claim 10 further comprising the step of forming a substantially discrete second pressure zone-sample interface at the orifice between the inner chamber and outer chamber.

12. A sampling apparatus consisting essentially of:
    (a) an inner tube having an inner orifice at one end which forms a pathway for sample flow away from the inner orifice;
    (b) a means for inducing sample flow through the inner orifice and through the pathway;
    (c) a middle tube having a middle orifice at one end and a closure at the other end through which the inner tube passes which forms an inner chamber that surrounds the inner tube and inner orifice;
    (d) a means for inducing pressure in the inner chamber;
    (e) a means for inducing sample flow through the middle orifice and through the inner chamber;
    (f) an outer tube having an outer orifice at one end and a closure at the other end through which the middle tube passes which forms an outer chamber that surrounds the middle tube and middle orifice; and
    (g) a means for inducing sample flow through the outer orifice and through the outer chamber.

* * * * *